United States Patent [19]

Ross et al.

[11] E Re. 30,926

[45] Reissued May 11, 1982

[54] ULTRASONIC INSPECTION

[75] Inventors: Benjamin J. Ross, Cleveland Heights; James M. Toth, Lyndhurst; Richard F. Abramczyk, Brunswick; Gerald R. Coy, Medina, all of Ohio

[73] Assignee: Republic Steel Corporation, Cleveland, Ohio

[21] Appl. No.: 231,758

[22] Filed: Feb. 5, 1981

Related U.S. Patent Documents

Reissue of:

[64] Patent No.: 4,195,530
Issued: Apr. 1, 1980
Appl. No.: 933,668
Filed: Aug. 14, 1978

[51] Int. Cl.[3] ..... G01N 29/04

[52] U.S. Cl. ..... 73/638; 73/644

[58] Field of Search ..... 73/618, 622, 627, 629, 73/633, 637, 638, 640, 642, 644; 310/322; 367/150

[56] References Cited

U.S. PATENT DOCUMENTS

| | | | |
|---|---|---|---|
| 2,984,756 | 5/1961 | Bradfield | 73/644 |
| 3,350,925 | 11/1967 | Coy | 73/640 |
| 3,663,842 | 5/1972 | Miller | 73/642 |
| 3,693,415 | 9/1972 | Whittington | 73/620 |
| 3,739,628 | 6/1973 | Saglio | 73/627 |
| 3,791,199 | 2/1974 | Toth et al. | 73/628 |
| 3,916,675 | 11/1975 | Perdijon | 73/642 |
| 3,924,453 | 12/1975 | Clark et al. | 73/642 |
| 3,933,026 | 1/1976 | Ham et al. | 73/622 |

*Primary Examiner*—Stephen A. Kreitman
*Attorney, Agent, or Firm*—Watts, Hoffman, Fisher & Heinke Co.

[57] ABSTRACT

An ultrasonic flaw detector for detecting irregularities in an object, such as a pipe, having a segment of annular cross-section. The detector includes a transducer with an involute transmitting surface for sending ultrasonic signals into the object at equal non-radial angles of incidence. The detector further includes transmission apparatus for maintaining a constant physical relationship between the transducer and the pipe and interpretive apparatus for correlating reflections of ultrasonic signals within the object with irregularities.

27 Claims, 7 Drawing Figures

ULTRASONIC INSPECTION

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to an ultrasonic flaw detecting device for determining abnormalities within a pipe or similar structure. Nondestructive ultrasonic testing of objects such as pipes is well known. With such testing an ultrasonic beam of energy is sent into an object by a transducer and detection of reflections or echoes off internal structure within the object permits determination of characteristics of that internal structure.

More particularly, if a piezoelectric crystal is pulsed with an electrical energy signal, that electric pulse causes an ultrasonic signal to be emitted. It is also known that if the ultrasonic signal reflects off an object within its path and returns to the piezoelectric crystal, that crystal responds by producing an electric signal. It is possible, therefore, to send ultrasonic signals into a test object whose internal structure is of interest and to develop information from crystal output signals which result from the reflections off the internal structure of the object.

2. Prior Art

Ultrasonic techniques for examining the internal structure of a pipe or other cylindrical objects are known. When the object of interest is a pipe and the area of interest within the pipe is a longitudinally extending weld area, it has been more effective in studying the internal structure of the pipe weld area to send the ultrasonic signals into the pipe transverse to the weld area rather than along its length.

One example of a proposed mechanism for determining the internal structure of a pipe or cylindrical object is the U.S. Pat. No. 3,924,453 to Clark et al. The angles of incidence of the ultrasonic beams into the pipe in the Clark device are unequal. If this technique of ultrasonic flaw detection is utilized, the correlation of flaw severity to reflected signal strength becomes difficult due to the non-monotonic variations in the strength of the received echo as a function of distance.

U.S. Pat. No. 3,693,415 to Whittington proposes another form of ultrasonic flaw detection for use with a cylindrical object. The Whittington patent teaches the use of an array of ultrasonic transducers which must be positioned about the pipe in a circular or cylindrical arrangement. Means must be provided for sequentially pulsing the transducers which make up this array in order that ultrasonic beams of the proper phase arrive at a given point in the pipe structure and then enter that structure to be reflected by flaws or irregularities within the pipe.

U.S. Pat. No. 3,916,675 to Perdijon proposes still another method for ultrasonically testing the internal structure of a cylindrical device. The Perdijon device, utilizes a complex deflector means which receives parallel ultrasonic beams from an ultrasound transducer and reflects these beams into the pipe structure. As can be seen by the complexity of the Perdijon proposal much care must be taken in designing the deflector means in order that the angle of incidence of the deflected beam strikes the pipe in the proper angle. The complex design required for the proper reflector shape must be repeated for pipes of different sizes and shapes and the complexity is significantly increased if any variation in detection capability is to be achieved.

SUMMARY OF THE INVENTION

The present invention comprises an ultrasonic flaw detector for scanning an annular section of an object whose internal structure is of interest. The use of a novel ultrasonic transducer design causes ultrasonic energy to enter the section and completely scan that section for flaws and irregularities. When a flaw exists within the section ultrasound energy is reflected from that flaw and returns along its incident path to the transducer where the reflected ultrasound energy is converted to electrical energy. Increased scanning reliability is achieved by causing the ultrasound energy to initially impinge the annular section of interest along a waveform whose angles of incidence with that section are substantially equal. Equal angles of beam incidence result in equal angles of beam refraction when the ultrasound enters the object of interest. If the angles of refraction are equal and the transducer dimensions properly determined, the ultrasonic beam will completely scan the interior of the annular section and no flaws will be missed.

Equal angles of incidence can be achieved by the utilization of an ultrasonic transducer device whose shape coincides or substantially coincides with that of an involute. An involute is a curve traced by the end of a taut string which when wound or unwound upon a fixed curve creates a certain configuration. In theory, the ultrasonic transducer surface could comprise a series of planar involutes of infinitesimal width which when summed together would create a surface involute. Engineering considerations, however, have dictated that instead of an actual involute being utilized, a portion of a circle is used in creating the transducer.

In designing the actual transducer surface three points are chosen on a theoretical involute and a circle is traced through those three points. The transducer which is actually constructed comprises a section of a cylinder the radius of which coincides with the radius of the circle which approximates a real involute.

It can be shown from geometrical considerations that if an ultrasonic beam's angles of incidence are to impinge upon an angular cross-section such as that of a pipe the involute must be generated from a generating curve or evolute which coincides with a circle. It can also be shown that the center of the circular evolute which generates the involute must coincide with the axis of the pipe to be scanned.

With the present invention the exact shape and size of the evolute, i.e., the generating curve is determined based on considerations of the pipe dimension to be studied. In determining the evolute's radius it is of primary importance to determine at what angle of incidence the ultrasonic beam is to be projected into the pipe. The two constraints of pipe radius and beam angle of incidence define a constant radius evolute for generating a theoretical transducer surface of the proper involute shape. From the theoretical transducer surface a quasi-involute which coincides with a portion of a circle is chosen and from that circle a cylindrical transducer surface is constructed.

A transducer surface in this configuration causes ultrasonic waves to impinge upon a pipe's surface with equal or substantially equal angles of incidence. When refracted within the pipe structure these waves tend to travel in paths which neither concentrate nor diffuse beam energy.

Equal angles of incidence also provide more uniform energy transferral to the pipe. It is known that varying the angle of incidence of the ultrasonic energy varies the amount of energy transmitted to the pipe. If the waveform incident on the pipe varies along its length in angle of incidence, the transmitted waveform therefore varies in the amount of energy transmitted through the pipe. This non-uniform energy distribution will provide non-uniform echo signals from pipe flaws which produce peaks and valleys in signal amplitude. The constant energy content of rays coming from an involute transducer provides a signal response which minimizes the peaks and valleys.

The transducer surface, once constructed, must be maintained in a proper geometric relationship with the pipe structure in order that the proper angles of incidence are maintained. To achieve this proper correlation between the transducer surface and the pipe surface a wedge structure which transmits ultrasonic beams is placed between the pipe and the transducer. To achieve the proper correlation the wedge structure is designed to contain two important surfaces. One surface coacts with the pipe structure and the other surface coacts with the ultrasonic transducer surface. The same quasi-involute used to construct the transducer can be used to create one wedge surface. For the other surface it is only necessary that the outside diameter of the pipe be known in order that the second surface of the wedge structure coincides with that diameter.

In addition to the constraints placed upon the shape of the transducer surface, a requirement exists with regard to a dimension of the transducer structure. In the embodiment of the transducer surface which comprises a segment of a cylinder, this dimension refers to the circumferential extent or size of the segment of the cylinder or the number of pi radians that segment intersects.

To understand this constraint one must examine the propagation of ultrasonic beams within the pipe structure. Once the ultrasonic beam enters the pipe it is refracted at the outer surface (the angle of refraction of course depends upon the refractive index of the wedge and pipe material) and then travels to the inside surface of the pipe. The angle of incidence on this surface is such that there is substantially total internal reflection. The ultrasonic beam of substantially undiminished energy is then transmitted again to the outside surface and again substantially totally internally reflected. Internal reflection continues for a number of reflections until the beam is gradually attenuated.

It can be seen that to be certain a flaw within the pipe structure is detected, the multiple reflections must cause the ultrasonic beam to sweep the entire section of interest within the pipe. If the quasi-involute surface is of an insufficient circumferential extent, it is conceivable that there will exist segments within the pipe structure which the ultrasonic beam never intersects. For this reason there is a minimum transducer dimension which insures the pipe to be examined is adequately swept by the reflected beams within that pipe structure. It also should be noted that any dimension beyond this minimum is excess and serves no useful function. Since the cost of fabricating the ultrasonic transducer surface increases as the size of the transducer increases, the minimum dimension should not be greatly exceeded.

If areas other than that in direct contact with the ultrasonic transducer are of interest the plexiglass wedge and transducer surface can be moved circumferentially about the pipe structure in order that other areas of the pipe structure are tested. Thus it is seen that the present invention does not require the design of an ultrasonic transducer surface which completely surrounds the pipe structure nor is a complex deflecting device necessary.

Accordingly one object of the present invention is to provide a flaw scanning device and method which completely scans an area of interest in an annular object. These and other objects, features and advantages of this invention become more apparent from the detailed description that follows when considered in connection with the accompanying drawings.

DETAILED DESCRIPTION

Figure 1:
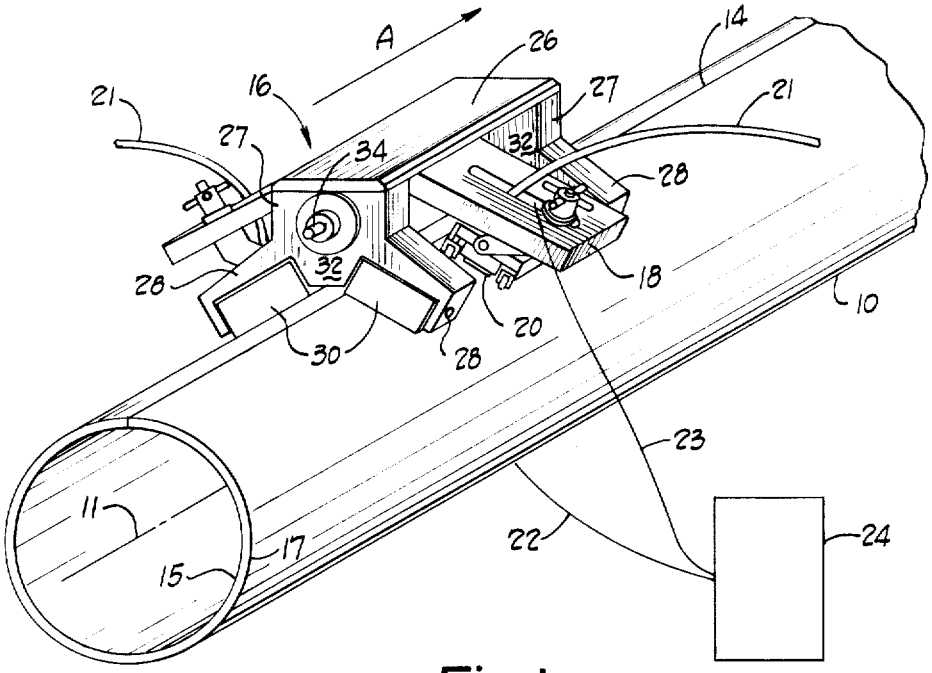
FIG. 1 is a perspective view of an ultrasonic flaw detector scanning a pipe section for flaws.

FIG. 1 shows the ultrasonic flaw detector assembly of the present invention positioned along a pipe 10. The pipe 10 has a center axis 11 and a longitudinal weld 14. It can be seen that the weld 14 forms a substantially straight line along a length of the pipe. The pipe has inside and outside surfaces 15, 17 whose spacing determine the thickness of the pipe to be scanned.

A detector mounting assembly or structure 16 is shown in FIG. 1 resting atop the pipe 10. This mounting structure is drawn along the pipe length in a direction indicated by the arrow A by any suitable means, not shown. Alternatively the pipe 10 is moved relative to the detector mounting structure 16 since relative motion is to be achieved.

The detector mounting structure 16 is an outrigger arrangement which includes a cross-member 26 which carries a pair of end pieces 32. Each end piece 32 includes a pair of outrigger arms 28, only three of which are visible in FIG. 1. Each outrigger arm 28, carries an outrigger roller 30. A rotatable mounting rod 34 extends between the two end pieces 32. Two detector mount arms 13 are mounted to this rod 34.

As relative motion of the pipe and detector occurs the outrigger crosspiece 26 maintains the four outrigger arms 28 in rigid relationship, one with the other. The detector mounting arms 18 on the contrary are rotatably mounted with the rod 34 and are arranged to rotate as the detector mounting structure encounters small variations in the pipe's surface. As the detector mounting structure 16 is drawn along the pipe in the direction indicated by arrow A, the outrigger rollers 30 are maintained in symmetric relationship to each other relative to the weld area 14. Thus, the assembly 16 is intended to be operated such that a plane located by the center axis 11 of the pipe and the weld area will bisect the rod 34.

Two ultrasonic transducer detecting devices 20 are mounted to the detector mount arms 18. As the ultrasonic detecting devices 20 move along the pipe 10 signals are sent from an electronic signal module 24 by means of two diagrammatically illustrated electrical interconnects 22 and 23. An electronic signal processor contained within the module sends signals to the ultrasonic transducer detecting devices 20 causing them to send ultrasonic sound waves into the pipe to scan for flaws and defects as the detecting mounting structure moves along the pipe. The electronic signal module 24 also interprets reflected signals from within the pipe structure when those signals rebound or echo off variations in density within the pipe structure. As will be seen with reference to FIG. 7, suitable means are connected to the electronic signal module to suitably mark the pipe at locations in which defects or flaws are found.

To ensure ultrasonic coupling between the transducer devices 20 and the pipe 10 a liquid coupling medium is provided by two hoses 21. These hoses typically provide a layer of water which is forced between the devices 20 and the pipe 10 to couple them for ultrasound transmittal.

By using two oppositely positioned transducers, each transducer can be tested by sending it a pulse from the other transducer. In this way proper coupling between pipe and transducer is assured. Also certain flaws may be difficult to detect for one transducer but due to the difference in orientation to the second transducer they will appear on that second device.

Figure 2:
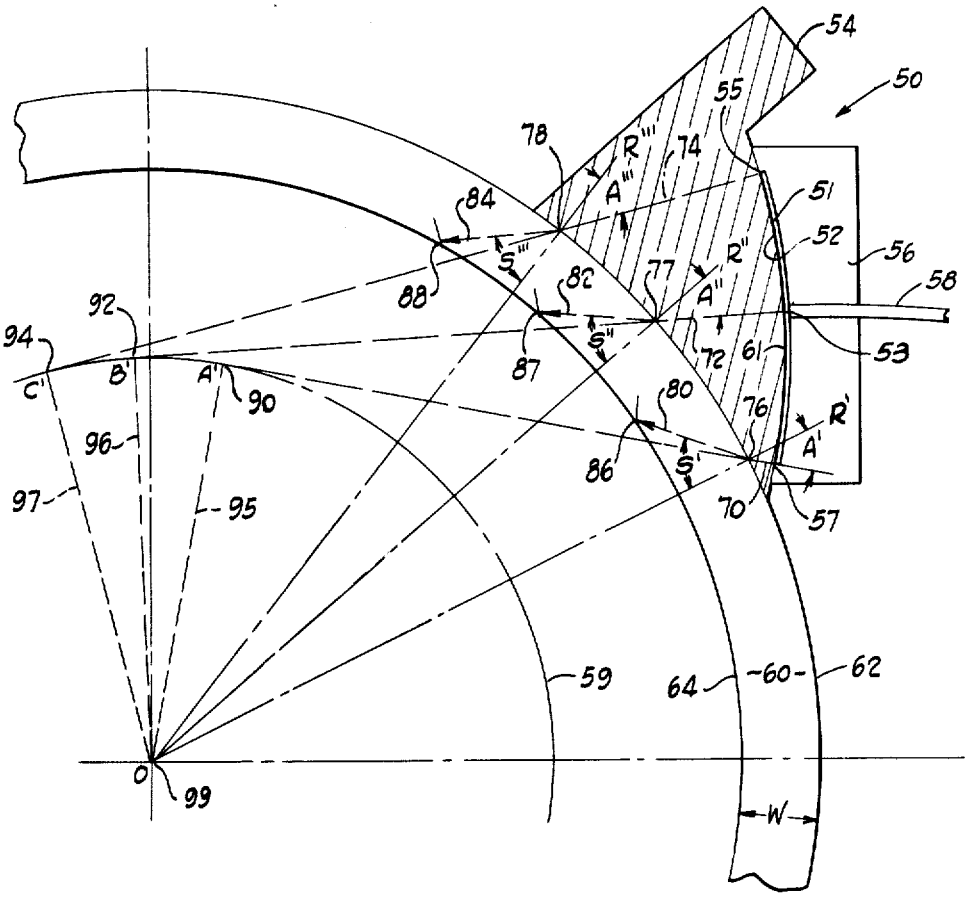
FIG. 2 is a cross-sectional view of an ultrasonic flaw detector in contact with a section of a pipe.

FIG. 2 is a schematic diagram of an ultrasonic flaw detector 50 with its mechanical mounting structure removed. The flaw detector 50 has an ultrasonic transducer 51 having a surface 52. The detector 50 also includes a sound transmitting wedge 54 which coacts with the surface 52, a transducer housing 56, and an electrical interconnection 58 attached to the transducer 51.

The wedge 54 is shown in direct contact with an outside surface 62 of a pipe 60. The wedge must be transmissive to sound and can be constructed from a synthetic acrylate resin such as that sold commercially under the trademark Lucite. Since the wedge 54 is in direct contact with the outside surface 62 of the pipe, the wedge obviously has one surface with a radius of curvature corresponding to the pipe outside surface's radius of curvature.

In operation, the signal module shown in schematic form in FIG. 1 sends an electrical signal along an electrical interconnect 58 to the transducer 51. The transducer is comprised of a material which upon receiving an electrical signal produces an ultrasonic sound energy wave over its surface 52. When the ultrasonic transducer receives an electrical signal from the electrical signal module, ultrasonic energy beams are transmitted through the wedge 54 until they impinge upon the pipe 60. It is accurate to speak of the ultrasonic energy as a volume of energy, but, for illustration purposes, the beam will be considered in a plane of cross-section referred to as a number of individual beam elements whose paths follow substantially straight lines.

Upon entering the pipe 60 the ultrasonic beams are refracted away from normal to the pipe surface and travel through the pipe searching for flaws or other irregularities in the pipe. If a flaw or irregularity is found, ultrasonic energy beam energy is reflected off that flaw and retraces its incident path to the ultrasonic transducer surface 52.

Ultrasonic beams travel from the transducer surface 52 along straight line paths and strike the outside surface 62 of the pipe. Typical incident beam elements indicated by the dashed lines 70, 72, 74 travel from the transducer 51 and strike the pipe 60 at exterior locations 76, 77, 78 along the pipe's outer surface 62.

When typical beam elements 70, 72, 74 strike the pipe surface they form angles of incidence A', A'' and A'''. Upon entering the pipe structure the individual ultrasonic beams are refracted away from the normal to the surface of the pipe along refracted beam paths 80, 82, 84 to form refraction angles S', S'' and S'''. These refracted beams travel through the pipe structure searching for flaws and irregularities until they reach internal points 86, 87, 88 located upon inside surface 64 of the pipe 60. If this refracted angle of incidence on the inside surface is greater than a critical angle (the definition of a critical angle is known within the art) there occurs substantially total internal reflection and the beams are sent from the inside toward the outside surface. The critical angle is dependent upon the index of refraction of the pipe and of the composition contained within the pipe. In the configuration shown in FIG. 1 the internal composition is air. The ultrasonic beams continue to bounce from the inside and outside surfaces of the pipe until gradually there occurs an attenuation which causes the beam strength to diminish.

As best seen in FIG. 2 the ultrasound producing transducer surface 52 comprises substantially an involute. A generating curve or evolute shown as a circle 59 is located coaxial with the pipe and has a diameter less than the pipe's inside surface 64. The transducer surface 52 is constructed such that for any point on its surface there exists an imaginary line to that point which intersects the evolute 59 at a point and in a direction tangent to that evolute. Choosing a point 53 in the mid-region of transducer surface 52 it is possible to trace a path 72 to the surface 52 that intersects the evolute 59 at a point 92. The path 72 intersects the evolute 89 in a direction that is perpendicular to a radius 96 to the point 92 of intersection. Similarly it can be seen that for other points 55 and 57 on the transducer surface 52 there exists perpendicular paths 70 and 74 that intersect evolute 59 at points 90 and 94 and with directions tangential to the evolute 59.

One method of tracing an involute comprises the technique of unwinding a string with a pencil or other marker at its end from around the generating curve or evolute. Thus, referring to FIG. 2 a taut string with a pencil or marker tied to its end could be wound around evolute 59. As the string is unwound it will coincide with the paths 70, 72 and 74 and the pencil would trace out the involute cross-sectional shape of the surface 52.

The size of angles of incidence A', A'', and A''' between the pipe 60 and the ultrasonic beams will depend upon the size of the generating circle or evolute 59. As the radius 95 of the evolute approaches the radius of the pipe's inside surface 64 those angles of incidence will increase. As the radius 95 of the evolute becomes smaller angles of incidence A', A'', and A''' will also become smaller. As the size of the evolute 59 approaches the limit of a point centered at the pipe axis the angles of incidence shrink to zero and the typical rays 70, 72, and 74 become radial to the pipe's outside surface 62.

It can be shown that regardless of the size of the evolute 59, as long as it comprises a circle, the angles of incidence A', A'' and A''' must be equal. In fact, any parts of an ultrasonic beam emitted by a transducer having a transducer surface generated by a circular evolute, will strike the annular cross-section of a pipe at equal angles along the outside surface of that pipe.

The proof of this proposition is straightforward. It requires the showing of congruency between two triangles shown in FIG. 2. One triangle contains vertices defined by the center 99 of the evolute, the point of tangency 90 to the evolute of a typical ray 70, and the point the ray 70 intercepts the pipe's outside surface 76. The second triangle contains vertices defined by the center 99 of the evolute, a second point 92 of tangency to the evolute and a second point 77 of interception of that tangency with the pipe's outside surface 62. By hypothesis the angles between the typical rays 70 and 72 and typical evolute radii 95 and 96 are right angles. Since radii 95 and 96 are radii to the same circle those sides of the two triangles are equal in length. Also the distance from the center of the evolute 99 to the two points of interception 77 and 76 are equal since they are merely the outside radius of the pipe 60. Therefore the two above defined triangles have two equal sides and one equal angle and therefore must be congruent. Since this is true the angle A'' defined by typical ray 72 and the normal to the pipe at the point 77 typical ray 72 intercepts the pipe must equal the angle A'' defined by a second typical ray 70 and the normal at the point 76 that ray 70 strikes the outer surface 62 of the pipe 64. This completes the proof that an involute will send typical beam rays to impinge upon the pipe with equal non-normal angles of incidence.

By utilizing equal angles of incidence A', A'' and A''' a detector made according to the present invention completely scans the pipe 60. It is instructure to examine the three typical beam paths 70, 72, 74 as they enter the pipe 60. These typical beams enter the pipe at points 76, 77, 78 which are equally spaced about the outside surface 62 of the pipe 60. That is, the circumferential distance between the lower point 76 and the midpoint 77 is approximately equal to the circumferential distance from the midpoint 77 to the uppermost point 78.

Upon entering the pipe the ultrasonic beam is refracted due to the different indexes of refraction of the pipe 60 and the wedge 54. Upon refraction typical beam paths 70, 72, 74 are bent to form equal angles of refraction S', S'' and S''', respectively. In traversing the pipe 30 the typical beams follow paths 80, 82, 84 and strike the inside surface 64 at nearly equally spaced points 86, 87, 88. Thus, the circumferential distance between the lower position 86 and the mid-position 87 is approximately equal to the circumferential distance between the mid-position 87 to the uppermost position 88. Thus, these typical beams tend to maintain their separation without diverging or converging as they travel throughout the pipe 60.

Figure 3:
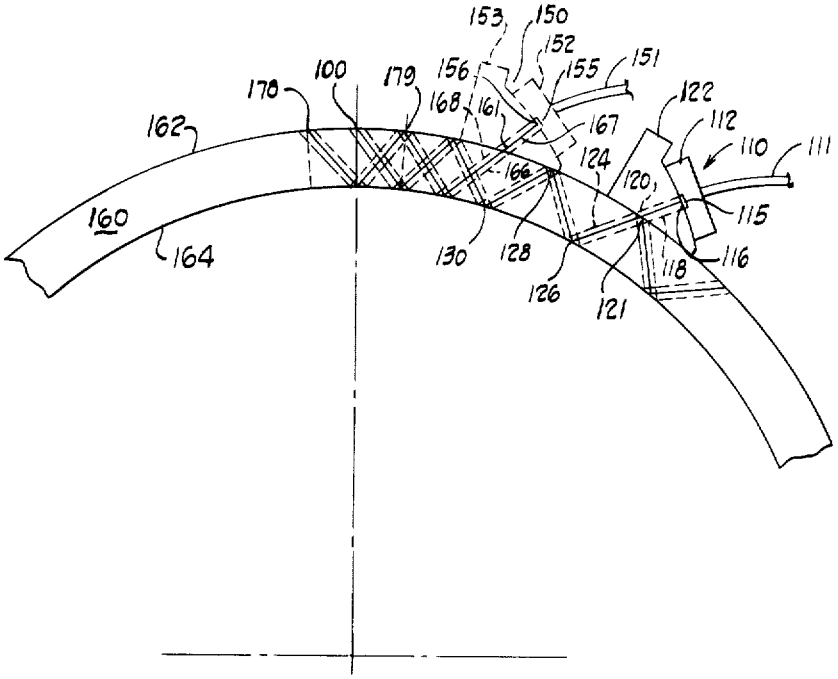
FIG. 3 is a diagrammatic sectional view showing two flaw detectors in different positions about the circumference of a pipe to be inspected.
Figure 4:
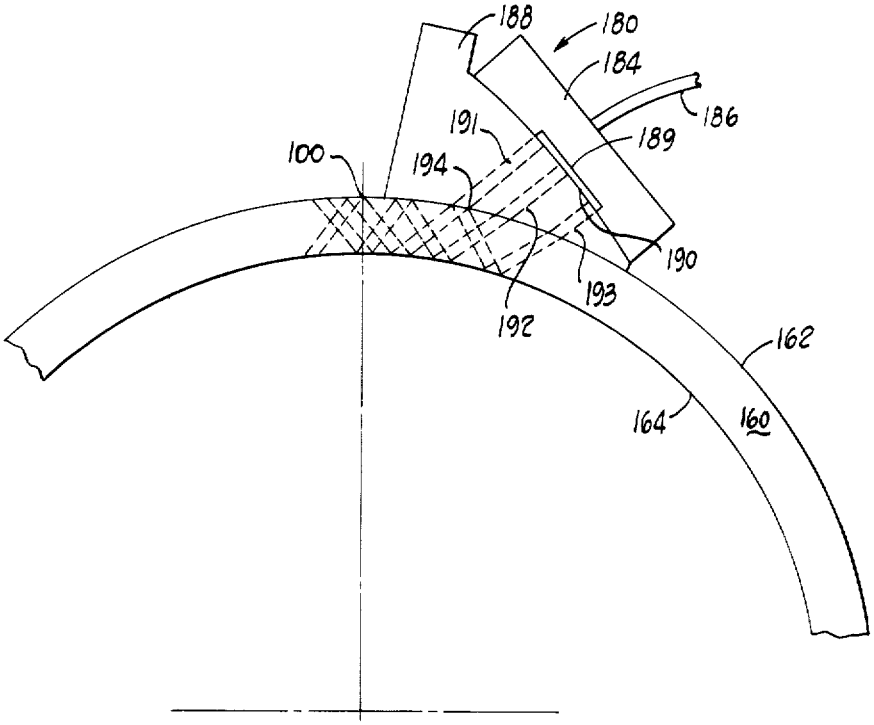
FIG. 4 shows a flaw detector whose circumferential length is adequate to scan the pipe shown in that figure.

If proper angles of incidence are chosen the beam paths 80, 82, 84 will strike the inside surface 64 at angles sufficiently large to result in nearly total internal reflection. As seen in FIGS. 3 and 4, if these angles of incidence are properly chosen the beam will enter the pipe and be reflected off the inside and outside pipe wall a number of times before they are attenuated. In one embodiment of the invention, incident angles of from 33 degrees to 45 degrees prove effective to achieve the required performance with an angle of incidence of approximately 35 degrees producing the best results. As noted previously it is possible to selectively choose the desired angle of incidence by changing the radius of the evolute or generating curve.

The preceeding geometrical proof and discussions of performance all relate to a transducer surface with a cross-section coincident with an involute. While engineering considerations do not preclude the possibility of the construction of an involute transducer surface they do suggest the use of a transducer surface which approximates an involute. In practice three points such as the three points 53, 55, 57 chosen in FIG. 2 are chosen on a real involute. Using these three points it is possible to construct a circle passing through these points which closely approximates the real involute. The circle in turn is the cross-sectional representation of a cylinder. The actual transducer comprises a segment of a cylinder whose cross-section coincides with a segment of that circle, three points of which coincide with an optimum involute shape. Although this quasi-involute or circle cannot produce exactly equal angles of incidence, the results approximate equal angles to the degree of accuracy required to adequately scan a weld area for flaws or irregularities.

FIGS. 3 and 4 show how ultrasonic scanning performance can vary depending on the physical dimensions of the transducer surface. The ultrasonic flaw detector 110 shown on the right in FIG. 3 is a schematic representation of a flaw detector constructed using the design described in FIG. 2. It comprises a transducer housing 112, a signal cable 111, a wedge 122 and a transducer 115 having a surface 116. The Lucite wedge 122 coacts with a pipe 160 having inside 164 and outside 162 surfaces. As shown in the figure, the size of the transducer surface 116 is small relative to the width of the pipe segment. The width of the ultrasonic beam propagating from the transducer is indicated by the two boundary ultrasound beams 118 and 120.

An ultrasound beam 124 emitted from the surface 116 travels to a location 121 on the outside surface 162 of the pipe 160 where it is refracted. The beam 124 then travels through the pipe 160 to a location 126 on the inside surface where nearly total internal reflection occurs. Similar internal reflections occur at locations 128, 130 along the pipe's cross-section. To illustrate these multiple reflections that can occur, the ultrasonic beam 124 as pictured is internally reflected five times before the beam strikes a flaw 100 and similarly rebounds five times before re-entering the Lucite wedge.

The transducer 115 is constructed of a piezoelectric crystal. This crystal exhibits the property that when it receives physical energy in the form of sound waves, it converts that energy to an electrical signal. Thus, when the wave retraces its incident path and strikes the transducer 115 an electrical signal is sent to a cable 111 which transmits that signal to a suitable electronic signal module (not shown in FIG. 3). Through electronic diagnostic techniques known within the art (and to be described) it is possible to deduce the existance and location of the flaw 100 within the pipe 160 through interpretation of the reflected signals.

As seen from the representation of the flaw detector 150 when moved to the left of FIG. 3, a narrow beam transducer surface may inadequately scan the entire pipe structure. The flaw detector 150 comprises a transducer housing 152, signal cable 151, Lucite wedge 153 and transducer 155 having a surface 156. The surface 156 produces an ultrasonic beam 167 with outermost boundaries 166, 168 defining a relatively narrow beam. The beam 167 enters the pipe at a location 161 on the outside surface 162 and is refracted. When the beam strikes the inside surface 164 total (or nearly total) internal reflection occurs and the beam continues its travel along the pipe's interior. Due to the narrow width of the beam 167, however, the beam never strikes the flaw 100. Instead the beam continues along its path until it is totally attenuated.

It is apparent from this discussion that in one position the detector 110 receives reflected signals from the flaw 100 and that in the second position the detector 150 receives no reflected signal from the flaw. Thus, an ultrasonic signal with width dimensions which are relatively too narrow for the pipe 160 may miss a flaw or irregularity in the pipe's internal structure.

As shown in FIG. 4 it is possible to construct an ultrasonic flaw detector 180 according to the present invention with a transducer 182 large enough to completely scan the pipe 160. It should be noted that the pipe 160 shown in FIG. 4 has the same inside 162 and outside 164 surface as the pipe shown in FIG. 3. The detector 180 comprises a transducer housing 184, cabling 186, a Lucite wedge 188 and an ultrasonic transducer 189 having a surface 190. Three typical ultrasonic beams segments 191, 192, 193 are schematically shown emerging from the transducer surface 190. If the ultrasonic beam is shortened to produce only one such beam 192 of width approximately equal to the beam width of FIG. 3, the flaw 100 might be missed as the beam inadequately scanned the pipe. With the transducer width increased to produce a beam defined by the two outside limits 191, 193 shown in FIG. 4, any change in density due to the existence of a flaw, regardless of its location within the pipe, will be detected. As seen in FIG. 4 either of two representative beam segments 191 or 193 will strike the flaw 100 producing a reflection which will return to the ultrasonic transducer and be interpreted by the electronic signal module. (Not shown in FIG. 4).

The two representative beam paths 191, 193 show the requisite conditions for adequate beam scanning for a given pipe dimension. If there exists one beam path 193 which is first reflected from the outside surface 162 at a point 194 within the boundary 191 of the incident ultrasonic energy then complete ultrasonic scanning will occur. Thus, in FIG. 4 either of the representative paths 191 or 193 will strike the flaw 100. Due to the non-converging and non-diverging nature of the beams, they will completely scan the pipe 160 in the vicinity of the detector 180 and will continue to scan as they travel in a circumferential direction about the pipe.

For pipe of a given outside and inside diameter it is possible to determine optimum transducer widths. It is apparent that as pipe thickness increases transducer width also must increase. For wall thickness of three-eights inch it has been determined that a transducer surface width of two inches scans the pipe for flaws. For other pipe thicknesses it is desirable to select transducer dimensions selected to scan as completely as desired for flaws or other irregularities within the pipe structure. Since due to engineering considerations an arc of a circle is used instead of a true involute, the circumferential extent of the arc is the dimension which is varied to match the thickness of the pipe to be scanned.

Figure 5:
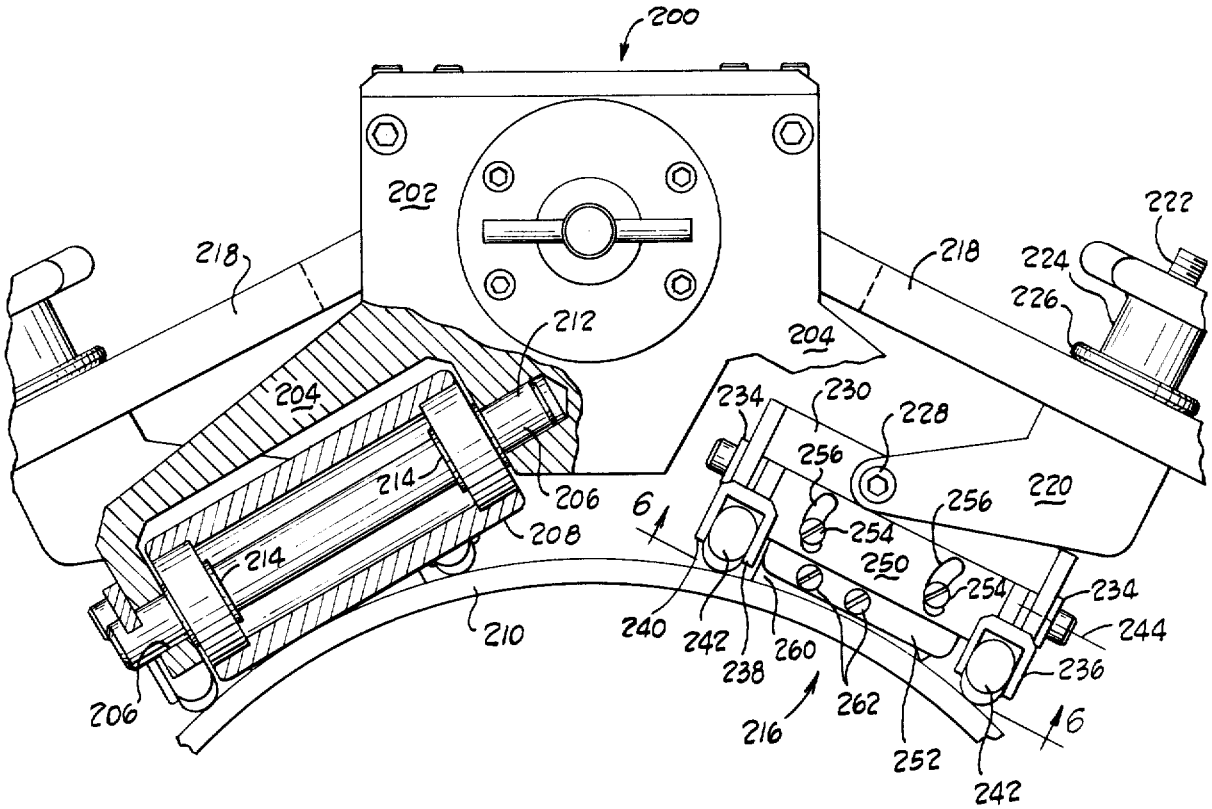
FIG. 5 shows an end elevational view with parts broken away and removed, of a flaw detector assembly that maintains its detector in close relation to a pipe to be scanned.
Figure 6:
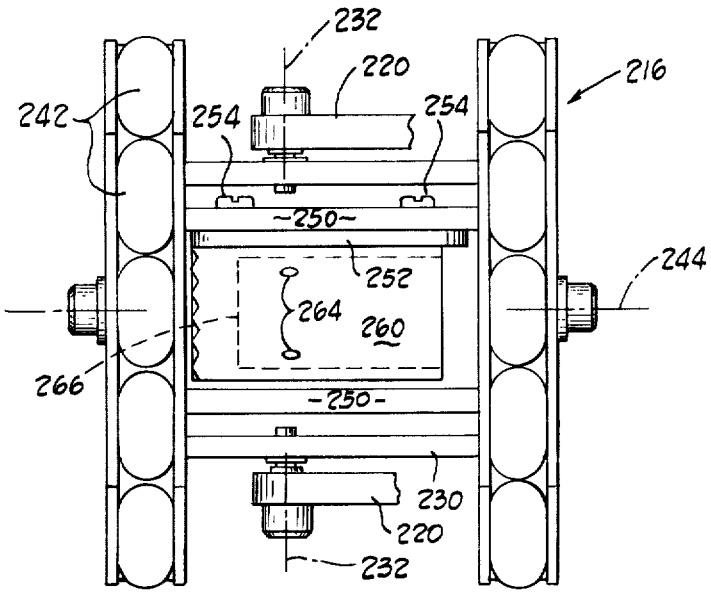
FIG. 6 shows a lower plan view from the pipe of the flaw detector assembly of FIG. 5.

Shown in FIGS. 5 and 6 is one method of mounting an ultrasonic transducer according to the present invention. FIG. 5 is an end view of the detecting mounting structure shown in less detail in FIG. 1.

An end piece 202 is provided which has two circumferentially extending outrigger arms 204. The outrigger arm 204 (on the left) has been partially sectioned to indicate how roller bores 206 carries a roller 208 for contact with the pipe 210. The roller 208 comprises a rodlike cross-member 212 which extends into the bores 206 found in the outrigger arm 204. By means of two bearings 214 the roller 208 rotates about the rodlike cross-member. The outrigger arm 204 is representative of the other three outrigger arms which are not shown in FIG. 5.

The outrigger arm 204 to the right in FIG. 5 has been broken away to show an ultrasonic detector mounting arrangemebt 216. This detector mounting arrangement is adjustably mounted to a detector mounting arm 218. The detector mounting arm 218 comprises a slotted arm which serves as a mount for two detector mounting brackets 220, only one of which is shown. A crosspiece not shown in FIG. 5 maintains the two detector mounting brackets 220 a fixed distance apart longitudinally of the pipe. Each mounting bracket has an attached threaded stud 222 which extends through the slot in the detector mounting arm 218.

The position of the bracket 220 relative to the arm 218 can be adjusted by unscrewing a threaded knob 224 which coacts with the threaded knob 222. The knob further acts against a tightening washer 226 which creates a friction joint with the slotted arm 218. When the knob 224 is loosened the friction joint between the arm 218 and the tightening washer 226 is lost and the bracket 220 may be moved along the detecting mount arm 218 circumferentially of the pipe to be inspected. When the proper adjustment is achieved the knob 224 is retightened and the frictional joint reestablished. The adjusting capability of the bracket 220 allows the ultrasonic testing device embodied by the present invention to be adjustably mounted upon pipes of different diameters.

The detector mounting bracket 220 carries a pivot 228. An intermediate mounting bracket 230 is pivotally mounted by the pivot 228. This pivot arrangement allows the intermediate bracket 230 to rotate about an axis 232 of the pivot 228 (FIG. 6). The ultrasonic detector is mounted to rotate with the intermediate bracket 230 about the axis 232 as a part of a gimbal arrangement to mount the ultrasonic detector.

A support member 234 is rotatably mounted to the intermediate bracket 230. Two shoe support members 236 are attached to the support member 234. Each shoe support member 236 comprises a U-shaped member with inner portion 238 and outer portion 240. These portions serve to maintain a number of sliding shoes 242 in fixed relationship to the shoe support member 236. These sliding shoes 242 rest upon the pipe and as the detector mounting structure 200 is drawn along the length of the pipe these shoes slide along the pipe and maintain the detector mount in the proper relationship to the pipe.

Each support member 234 is rotatably mounted on its intermediate bracket 230 for rotation about an axis 244 perpendicular to the axis 232. This rotational axis is the second axis of the gimbal arrangement for the shoe support members 236. Thus, the member are free to rotate about two axes to allow the supporting shoes 242 to contact the pipe regardless of variations in the pipe.

The ultrasonic flaw detector is mounted within a detector mount 250. The detector mount 250 is rigidly attached to the shoe support member 236. A transducer housing structure 252 is adjustably mounted within the detector mount 250. The position of the transducer housing structure 252 relative to the detector mount 250 can be adjusted until the mount's relationship to the pipe is optimum for sending ultrasound waves with equal angles of incidence into the pipe.

A first pair of screws 254 coact with two slots 256 within the detector mount 250. These screws 254 are screwed into the transducer housing structure and can be loosened and their position adjusted by sliding them along the two slots. Once this adjustment has been made for a particular pipe these screws are tightened and the transducer housing structure remains fixed relative to the detector mount.

A Lucite wedge 260 is interposed between the transducer, which is mounted to the transducer housing, and the pipe. Since the shape of the Lucite wedge like the transducer depends on the pipe to be scanned, means are provided for removing the wedge and replacing it with a wedge of different shape. The Lucite wedge 260 is attached to the transducer housing structure 252 by means of two countersunk screws 262.

When pipes of different dimensions are to be scanned a new transducer is mounted within the housing 252 by any suitable means to maintain the housing and the transducer in constant physical relation to one another. The first pair of screws 254 are then adjusted to maintain the transducer surface (not shown in FIG. 5) in proper relation to the pipe 210. When this is done, a proper Lucite wedge with a radius curvature the same as the pipe under study is attached to the housing 252 by the countersunk screws 262.

FIG. 6 shows the mounting arrangement 216 as seen from the surface of the pipe. There are five sliding shoes 242 on either side of the transducer housing structure 252. Although the countersunk Lucite mounting screws cannot be seen from this view, the Lucite wedge 260 can be seen attached to the transducer housing structure. Located near the sides of the Lucite wedge 260 are water spouts 264 through which water is sprayed. This water serves to ultrasonically couple the Lucite wedge 260 to the pipe 210. Typically a gap between 0.010 to 0.035 inches is maintained between the wedge and the pipe wall. Water is forced through the spouts to fill this gap to couple the wedge to the wall. The water may contain additives, such as aerosol which act as wetting agents.

An ultrasonic transducer surface 266 corresponding to those which have been described in detail, is shown in phantom in FIG. 6. While the description of FIG. 2 characterized the surface as an involute, or as a quasi-involute, the view from the pipe is one of a rectangular transducer. The longer of the two sides are actually involute or quasi-involute in shape. The shorter of the two sides are lines in both this view and in any other possible view of the transducer surface. In one embodiment used for testing, a pipe whose inside and outside surfaces form a 2 inch cross-section, the dimension of this rectangular transducer is $1\frac{1}{4} \times 2\frac{1}{4}$ inches.

Figure 7:
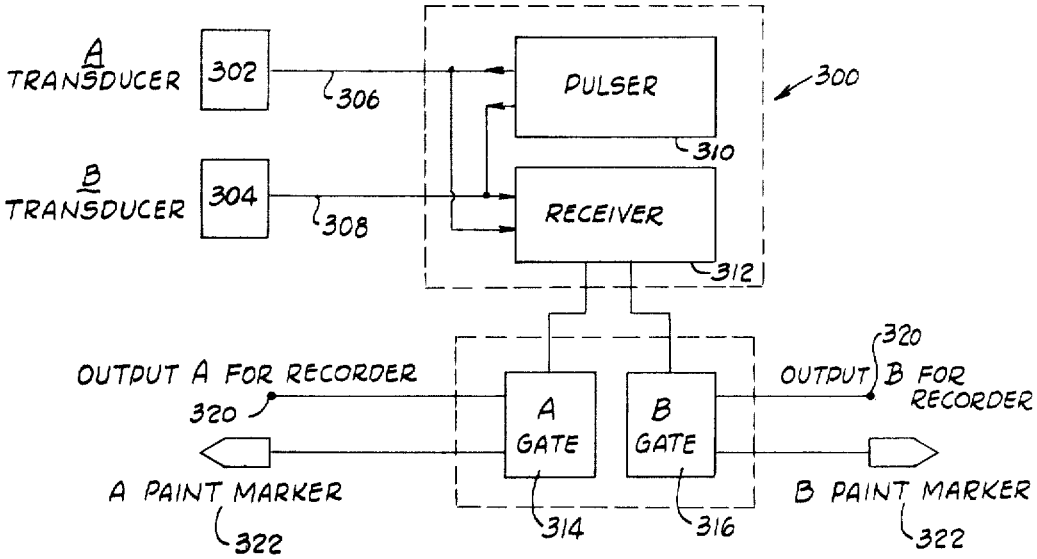
FIG. 7 shows a schematic electrical diagram of the electronics for controlling the sending and receiving of ultrasonic signals.

As the detector mounting structure 216 travels along the pipe, the transducer mounted within the detector mount 250 emits ultrasonic signals which scan the pipe for irregularities within the weld structure. The timing of these emitted signals is controlled by the electronic signal module 24 of FIG. 1. A block diagram illustrating a typical circuit 300 which might be used for controlling the sending and receiving of signals by the ultrasonic transducer is shown in FIG. 7. The circuit 300 is electrically connected to two transducers 302, 304 by means of electrical interconnects 306, 308. These two transducers correspond to the two transducers arranged on either side of the pipe as shown in FIG. 1.

The transducers are activated by an activation signal which is sent from a pulser circuit 310. The pulser circuit 310 is located within the electronic signal module and connected to each of the two transducers. The electrical energy sent from the pulser is converted to ultrasonic energy by the transducers.

As the emitted signal rebounds off flaws or irregularities within the pipe structure the returning or reflected signals impinge upon the transducer and are reconverted to electrical signals. These return signals return along cabling 306, 308 to a receiver unit 312. These returned electrical signals are processed by the receiver and sent to a gating circuit 314 or 316 which sends a signal by means of electrical interconnection to a recording device which records the existence of the flaw or defect within the pipe. The system shown in FIG. 7 includes a redundant recording system which includes both a strip chart recorder 320 and a paint marker 322 for marking the pipe surface with a paint spot at the site of the flaw.

The signal sent from the pulser 310 to the transducers 302, 304 is an electronic pulse which resembles a voltage spike followed by a damped voltage sine wave. The damped portion of the signal is due to ringing within the circuit.

Due to the positioning of the two transducers it is necessary that the pulsers alternate their activating signal to insure the signal from one (for example 302) does not adversely affect the receiving of the ultrasonic energy by the other 304. If for example both transducers were simultaneously activated by the pulser unit the transducers would not know whether they were receiving a reflected signal from a flaw or defect within the weld structure or whether they were merely receiving a transmitted wave from the other of the two transducers. To properly sequence the transducer activation, a pulser unit contains a sequencing device which is controlled by a triggering device. The trigger device acts as a clock or time reference within the pulser unit and the sequencer alternately activates the two transducers to produce the ultrasonic sound waves of the present invention.

Pulsers such as the one mentioned above are known within the art. One commercially available device is a Krautkramer-Branson, Inc. unit which includes a Model TG1 triggering unit and a Model PSI sequencer. This unit uses two SD4 transmitter devices which are powered by a NE2 power supply module. It is the NE2 or an equivalent power supply which provides energy for the remaining elements of the electronic signal module to be described.

As noted in FIG. 7 both transducers are electrically connected to a receiver unit 312. The two primary functions of the receiver 312 are to amplify and shape the signals from the transducers 302 and 304. The typical reflection signal from a flaw within the weld area causes the transducer to produce an envelope of RF signals of fairly small voltage. In order for the subsequent recording apparatus to respond to these signals they must be significantly amplified. Since the recording devices 320 and 322 most conveniently respond to pulses or spikes, the amplified RF envelope must also be shaped to achieve a single pulse of approximately 5 microseconds.

Circuitry for achieving this requisite pulse is known within the art. A Krautkramer-Branson, Inc. Model ANS 11 and ANS 1, for example, operate as amplifiers in one typical receiving unit. A TA1 distance amplitude correction unit should also be included to automatically correct for changes in reflected beam amplitude due to naturally occurring attenuation within the pipe. This TA1 unit automatically corrects for this attenuation and therefore provides a uniform signal for the gating circuitry 314, 316.

The gating circuitry 314, 316 receives signals from the reflected ultrasound energy regardless of whether the flaws producing these signals are inside the weld area. In the disclosed embodiment, essentially only flaws within the weld area are of interest to the user. The gates 314, 316 serve to block out signals coming from flaws or irregularities outside of the weld area. This capability is achieved through a knowledge of how long it takes the pulse to reach the weld area and to return to the transducer.

Considering FIG. 3, for example, the weld area may be a range indicated by two boundaries 178, 179 surrounding the defect 100 as shown in that figure. Utilizing knowledge of how rapidly the ultrasonic beam travels through the pipe, it is possible to program the gating circuitry 314, 316 of FIG. 7 to allow signals to activate the recording means only after an initial delay during which time any reflected signals must be coming from outside the weld area. If, for example, the gating circuitry allowed earlier signals to activate the recording apparatus, irregularities to the right of the boundary area 179 in FIG. 3 will be detected. These irregularities are of little interest to the user in this application and therefore are not allowed to control the recording devices 320 or 322. In a like manner irregularities to the left of the leftmost weld boundary 178 are of little interest. The gating circuitry therefore is operative to activate the recording circuitry for only a short period of time during which the reflected signals will be coming from within the weld area.

A gating circuit with the above mentioned capabilities is a Model No. BL1 produced by Krautkramer-Branson, Inc. This circuitry is adjustable to allow for inspection of pipes of varying diameters and differing transducer placements relative to the pipe weld structure. As an illustration, in one embodiment the BL1 gating circuits are closed and allow no signals to reach the recording device for a period of 50 microseconds. These circuits then open and allow reflected signals to activate the recording device for a period of 20 microseconds. During this 20 microsecond open period the reflected signals would have been scanning the weld area and are of interest to the user. The BL1 then closes and disregards any returning signals which would be coming from areas beyond the weld structure and therefore of no interest.

During the period in which the gates 314, 316 send received signals to a recording device, they also operate to shape and lengthen the pulse sent by the receiver. In a typical example the 5 microsecond pulse sent by the receiver may be lengthened to a 30 millisecond pulse which is operative to control the recording devices.

The circuitry of FIG. 7 can be used to activate a series of different recording devices all of which indicate the presence of a flaw in the weld area. As shown in FIG. 7 apparatus 320 may be provided for recording permanently upon a strip chart recorder the presence of a flaw within the weld structure. It is also possible to connect the gating circuitry to a paint marking device 322 which automatically produces a spot of paint on the pipe in the area of the weld flaw. A cathode ray tube mounted upon a viewing device might also be used to produce a representation indicative of a flaw in a workpiece.

As examples of devices known within the art to produce these results, one could choose a TO1 model by Krautkramer-Branson, Inc. to activate the painting device, an RV1 model by the same manufacturer to activate the strip chart recorder, and a PS1 sequencer again by the same manufacturer could be used as an oscilloscope CRT device for providing directly readable signal indicating the presence of a flaw.

While the present has been described with particularity, it should be understood that various modifications and alterations may be made therein without departing from the spirit and the scope of the invention set forth in the appending claims.

What is claimed is:

1. An ultrasonic flaw detector for detecting irregularities in an object having at least a segment of an annular cross-section such as a pipe comprising:

(a) a transducer for sending a wave of ultrasonic energy into such object; said transducer being configured such that at any given point in a plane of transverse object cross-section the energy impinges such object at a non-radial angle of incidence substantially equal to the angle of incidence of every other point in the plane;

(b) transmission means including a first surface coacting with said transducer to insure said transducer maintains a substantially constant physical relationship with said object while transmitting said energy to the object; and (c) interpretive means to correlate reflections of said ultrasonic signals with irregularities in the structure of said object.

2. The ultrasonic flaw detector of claim 1 where a cross-section of said first surface comprises an involute characterized by a generating circle whose center coincides with the axis of an object to be inspected.

3. The ultrasonic flaw detector of claim 1 wherein the transducer comprises a detecting-transmitting piezoelectric crystal.

4. The ultrasonic flaw detector of claim 2 wherein the transmission means comprises a Lucite wedge with a second surface coacting with said object.

5. The ultrasonic flaw detector of claim 1 wherein a cross-section of said first surface approximates an involute generated by a circular evolute.

6. The ultrasonic flaw detector of claim 5 wherein said surface is a portion of a cylinder and where said cross-section comprises an arc of a circle three points of which coincide with an actual involute.

7. An ultrasonic flaw detector for detecting irregularities in an object with annular cross-section comprising:

(a) a transducer including a signal emitting surface for sending a wave of ultrasonic energy to said object; said transducer configured such that at any point in a plane of transverse object cross-section the wave impinges said object at non-radial angles of incidence substantially equal to the angles of incidence of every other point in the plane;

(b) a transmission means coacting with said surface and transmitting ultrasonic signals to said object; and (c) means attached to said transducer for correlating reflections of said ultrasonic signals with the structure of said object.

8. The ultrasonic flaw detector of claim 7 wherein a cross-section of said surface coincides with an involute characterized by a circular evolute whose center coincides with the axis of the annular cross-section to be inspected.

9. The ultrasonic flaw detector of claim 8 wherein the transmission means comprises a Lucite wedge with a first wedge surface coacting with said cylindrical object and a second wedge surface coacting with said involute.

10. The ultrasonic flaw detector of claim 7 wherein said surface comprises a segment of a cylinder; a cross-section of said cylinder comprising a segment of a circle, three points of which coincide with three points on an involute whose generating curve comprises a circular evolute.

11. A method for scanning a workpiece having an annular section such as a pipe or a pipe weld area comprising the steps of:

(a) fabricating an ultrasonic transducer surface shaped such that a plane cross-section parallel to the annular section intercepts said transducer along an involute;

(b) pulsing said transducer with an electrical signal thereby producing an ultrasonic waveform whose individual components travel to said workpiece along different straight line paths; said components impinging upon said object at substantially equal non-radial angles of incidence; and (c) correlating reflections of said waveform from said object with irregularities within said object's structure.

12. The method of claim 11 which further comprises the step of interposing a transmission means between said transducer and said object to maintain the desired spatial relation between said transducer and said object without significantly attenuating said waveform.

13. The method of claim 12 wherein said transmission means comprises a Lucite wedge and said ultrasonic transducer comprises a piezoelectric crystal.

14. The method of claim 13 wherein said ultrasonic transducer surface comprises a four-edge figure; two of said edges comprising involutes and two of said edges comprising straight lines.

15. A method for scanning a pipe weld area for weld defects and structural irregularities comprising the steps of:

(a) fabricating an ultrasonic transducer surface with a cross-section whose shape corresponds with a circle; at least three points of said circle coinciding with three points on an involute; said involute generated by a circular generating evolute whose center coincides with the center axis of said pipe;

(b) placing said surface in close relation to said pipe and causing relative pipe and surface movement;

(c) pulsing said ultrasonic transducer surface with repetitive electronic signals thereby causing ultrasonic energy beams to be transmitted toward said pipe;

(d) coupling said surface to said pipe with a translucent media; said media operative to maintain said surface and said pipe in a substantially constant physical relationship thereby insuring said beams enter said pipe with substantially equal angles of incidence; and (e) interpreting electrical signals from said ultrasonic transducer produced by ultrasonic beam reflections within said pipe which have reflected off a density variation within said pipe indicative of a structural irregularity.

16. An ultrasonic flaw detector for detecting irregularities in an object having at least a segment of an annular cross section comprising:

(a) a transducer including a signal emitting surface which approximates a segment of a cylinder; a cross section of said cylinder intercepting three points on a circle which coincide with three points on an involute whose generating curve comprises a circular evolute;

(b) transmission means coacting with said surface and transmitting ultrasonic signals to said object; and (c) electronic means attached to said transducer for correlating reflections of said ultrasonic signals with the structure of said object.

17. The flaw detector of claim 16 wherein the transmission means defines two surfaces; a first surface coacting with said transducer and a second surface coacting with said object; and where said first and second surfaces include cross sections with approximate circles.

18. The flaw detector of claim 17 wherein the transmission means defines a path for supplying a fluid for ultrasonically coupling said second surface and said object.

19. An ultrasonic flaw detector for detecting flaws in a weld area of a pipe comprising:

(a) a transducer including a signal emitting surface with a cross section approximating an involute with a circular generating curve;

(b) pulse generating means for energizing said transducer and thereby transmitting ultrasonic energy to said pipe;

(c) transmission means including a first surface with approximately involute cross section coacting with the transducer and a second cylindrical surface coupled to the pipe; said transmission means comprising an ultrasonic transmissive material attached to said transducer to maintain the transducer in relation to said pipe; and (d) electronic circuitry coupled to said transducer for correlating reflections of ultrasonic energy with flaws in the weld area.

20. The flaw detector of claim 19 wherein the transmission means defines a path for providing an ultrasonic coupling fluid between the cylindrical surface and the pipe.

*21. A method for scanning a workpiece having an outer surface including at least a segment which is generally cylindrical and defines an axis, such as a pipe or pipe weld area, said method comprising the steps of:*

*(a) positioning proximate the workpiece an ultrasonic transducer having an emitting surface shaped such that a plane perpendicular to the axis intercepts the emitting surface along an involute;*

*(b) pulsing said transducer with an electrical signal for providing an ultrasonic waveform, which waveform impinges upon the exterior surface of the workpiece at substantially equal incident angles nonradially with respect to the workpiece, and*

*(c) correlating reflections of said waveform from said object with irregularities within said object structure.*

*22. The method of claim 21, further comprising the step of interposing a transmission means between the transducer and the workpiece to maintain a desired spatial relation between the transducer and the workpiece without significantly attenuating the waveform during its passage to the workpiece.*

23. The method of claim 22, wherein said interposing step comprises interposing a transmission means comprising a lucite wedge, and in which said positioning step comprises positioning an ultrasonic transducer including a piezoelectric crystal.

*24. The method of claim 23, wherein said positioning step further comprises positioning an ultrasonic transducer having a surface defining a four edged figure, two of said edges defining involutes and two of said edges defining straight lines.*

*25. A method for scanning a workpiece having a generally cylindrical outer surface defining an axis, such as a pipe or a pipeweld area, said method comprising the steps:*

*(a) positioning an ultrasonic transducer proximate the workpiece, said transducer defining a cross section perpendicular to said axis corresponding with part of a circle, at least three points of said circle coinciding with three points on an involute, said involute being defined as generated by a circular generating evolute concentric with said axis;*

*(b) causing relative pipe and transducer movement;*

*(c) pulsing said transducer with repetitive electrical signals for causing ultrasonic energy to be transmitted toward the workpiece;*

*(d) coupling the emitting surface of the transducer to the workpiece with a coupling medium, to maintain the emitting surface and the workpiece in a substantially constant physical relationship for maintaining the ultrasonic energy incident on the outer surface of the workpiece at substantially equal angles of incidence, and*

*(e) interpreting electrical signals from the ultrasonic transducer produced in response to ultrasonic energy reflections within the workpiece which have reflected from a density variation within the workpiece indicative of an internal structural irregularity.*

*26. An apparatus for detecting flaws in a workpiece defining at least a segment of a generally cylindrical outer surface having an axis, said apparatus comprising:*

*(a) an ultrasonic transducer having a generally concave emitting region at least approximately defined by a set of lines substantially parallel to said axis;*

*(b) structure for holding said transducer proximate the workpiece during operation with normals defined by its emitting region extending into the workpiece without intersecting said axis;*

*(c) circuitry for electrically pulsing the transducer for propagating ultrasonic energy to the workpiece along said normals, and*

*(d) interpretive circuitry responsive to ultrasonic echoes from within the workpiece to indicate the existence of a workpiece flaw.*

*27. An ultrasonic inspection apparatus for detecting flaws in a workpiece having an outer surface including at least a segment which is generally cylindrical and has an axis, said apparatus comprising:*

*(a) an ultrasonic transducer having a generally concave curved emitting surface defined by a set of lines parallel to said axis;*

*(b) mounting structure for holding the transducer proximate the workpiece during operation with normals defined by the emitting surface extending into the workpiece without intersecting said axis.*

* * * * *